(12) United States Patent
Tanaka et al.

(10) Patent No.: US 8,101,594 B2
(45) Date of Patent: *Jan. 24, 2012

(54) METHOD FOR IMPROVING PANCREATIC FUNCTIONS

(75) Inventors: Miyuki Tanaka, Zama (JP); Eriko Misawa, Zama (JP); Noriko Habara, Zama (JP); Muneo Yamada, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/576,652

(22) PCT Filed: Feb. 28, 2006

(86) PCT No.: PCT/JP2006/303709
§ 371 (c)(1),
(2), (4) Date: Apr. 4, 2007

(87) PCT Pub. No.: WO2006/123465
PCT Pub. Date: Nov. 23, 2006

(65) Prior Publication Data
US 2008/0255077 A1 Oct. 16, 2008

(30) Foreign Application Priority Data
May 17, 2005 (JP) .................. 2005-144385

(51) Int. Cl.
*A01N 43/00* (2006.01)
(52) U.S. Cl. ................... 514/183; 552/547
(58) Field of Classification Search .............. 514/183; 552/547
See application file for complete search history.

(56) References Cited

U.S. PATENT DOCUMENTS

| | | | |
|---|---|---|---|
| 4,598,069 A | 7/1986 | Hikino et al. | |
| 5,494,907 A | 2/1996 | Nique et al. | |
| 6,573,299 B1 | 6/2003 | Petrus | |
| 2005/0175745 A1* | 8/2005 | Zawistowski | 426/321 |
| 2007/0032463 A1* | 2/2007 | Higuchi et al. | 514/169 |

FOREIGN PATENT DOCUMENTS

| | | |
|---|---|---|
| CN | 1458918 A | 11/2003 |
| EP | 1 125 584 | 8/2001 |
| JP | 60-214741 | 10/1985 |
| JP | 05-247086 | 9/1993 |
| JP | 09-040689 | 2/1997 |
| JP | 10-330266 | 12/1998 |
| JP | 2003-048837 | 2/2003 |
| JP | 2003-113111 | 4/2003 |
| JP | 2003-286185 | 10/2003 |
| RU | 2 140 423 | 10/1999 |
| RU | 2 192 876 | 11/2002 |
| WO | WO 97/17086 | 5/1997 |
| WO | WO 99/19505 | 4/1999 |
| WO | WO 03/037360 | 5/2003 |
| WO | WO 2004/067009 | 8/2004 |
| WO | WO 2004067009 A1 * | 8/2004 |
| WO | WO 2004/105770 | 12/2004 |
| WO | WO 2005/094838 | 10/2005 |

OTHER PUBLICATIONS

Effect of Aloe Vera extract on some Physiological parameters in diabetics albino rats (The Egyptian Journal of Hospital Medicinevol. 12 12:53-61.*
Miyuki Tanaka et al. (Identification of five phytosterols from aloe vera gel as anti-diabetic compounds, Biol. Pharm. Bull 29 (7) 1418-1422 (2006)).*
Babak et al "Chronic pancreatitis: diagnosis, classification, and new genetic developments", Gastroenterology, 2001, vol. 120, pp. 682-707.*
Duell et al "A population-based study of the Arg399gln polymophism in X-ray repair cross-complementing group 1 (XRCC1) and risk of pancreatic cancer", Cancer research, vol. 62, pp. 4630-4636, Aug. 2002.*
Gura, Science, v278, 1997, pp. 1041-1042.*
Furong Wang et al "Diabetes Mellitus and Pancreatic cancer in a population-based case-control study in the San Francisco Bay are, California", Cancer Epidemiol. Biomarker Prev 2006, vol. 15, No. 8, pp. 1458-1463.*
Feng Want et al "The relationship between diabetes and pancreatic cancer", Review, Biomed central, Jan. 6, 2003.*
Kimattila et al "In vivo glucose-stimulated amylin secretion is increased in nondiabetic with pancreatic cancer", Metabolism, voll. 50, Issue 9, Sep. 2001, pp. 1036-1042.*
Miettinen, et al. "Low Synthesis and High Absorption of Cholesterol Characterize Type 1 Diabetes," *Diabetes Care*, vol. 27, No. 1, pp. 53-58, Jan. 2004.
Abou Zeid, A.H.S., Chemical and Biological Study of the Leaves of Some *Musa* Species, *Egypt. J. Pharm. Sci.*, vol. 39, Nos. 4-6, pp. 379-398, 1998.
Yeh, et al. "Systematic Review of Herbs and Dietary Supplements for Glycemic Control in Diabetes," *Diabetes Care*, vol. 26, No. 4, pp. 1277-1294, Apr. 2003.
International Search Report dated Apr. 24, 2006.

(Continued)

*Primary Examiner* — Brandon Fetterolf
*Assistant Examiner* — Jean Cornet
(74) *Attorney, Agent, or Firm* — Knobbe, Martens, Olson & Bear, LLP

(57) ABSTRACT

Compounds such as 4-methylcholest-7-en-3-ol, 4-methylergost-7-en-3-ol and 4-methylstigmast-7-en-3-ol which have an activity for improving pancreatic function are used as an active ingredient of a pancreas function improving drug and food or drink.

1 Claim, No Drawings

OTHER PUBLICATIONS

Bunyapraphatsara, et al., "Antidiabetic Activity of *Aloa vera* L. juice II. Clinical Trial in Diabetes Mellitus Patients in Combination with Glibenclamide," *Phytomedicine*, vol. 3, No. 3, pp. 245-248, 1996.

Beppu, et al. "Hypoglycaemic and Antidiabetic Effects in Mice of *Aloe arborescens* Millar Var. *natalensis* Berger," *Phytotherapy Research*, vol. 7, pp. S37-S42, 1993.

Okyar, et al. "Effect of *Aloe vera* Leaves on Blood Glucose Level in Type I and Type II Diabetic Rat Models," *Phytotherapy Research*, vol. 15, pp. 157-161, 2001.

Yongchaiyudha, et al. "Antidiabetic Activity of *Aloe vera* L. juice. I. Clinical Trial in New Cases of Diabetes Mellitus," *Phytomedicine*, vol. 3, No. 3, pp. 241-243, 1996.

Jeong, et al. "α-Spinasterol Isolated from the Root of *Phytolacca americana* and its Pharmacological Property on Diabetic Nephropathy," *Planta Med*, vol. 70, pp. 736-739, 2004.

Furukawa, et al. "Chemopreventive Effects of *Aloe arborescens* on N-nitrosobis(2-oxopropyl)amine-induced Pancreatic Carcinogenesis in Hamsters," *Cancer Letters*, vol. 178, pp. 117-122, 2002.

Rajasekaran, et al. "Hypoglycemic Effect of *Aloe vera*, Gel on Streptozotocin-Induced Diabetes in Experimental Rats," *Journal of Medicinal Food*, vol. 7, No. 1, pp. 61-66, 2004.

"Testbericht Spinnrad Aloe Vera Gel Bodylotion," internet citation retrieved from http://www.yopi.de/rev/164033 on Aug. 31, 2010.

Mohammad Azam Khan; Muheet-e-Azam, vol. IV (Part I) (19th century AD), Matba Nizami, Kanpur, 1899 AD, p. 175, Formulation ID: FA1/328B, Formulation Name: Maghz-e-gheekawar/sibr.

Mohammad Azam Khan; Muheet-e-Azam, vol. IV (Part I) (19th century AD), Matba Nizami, Kanpur, 1899 AD, p. 175, Formulation ID: FA1/328E1, Formulation Name: Nuskha-e-zulal.

Mohammad Najmul Ghani Khan; Khazaain-al-Advia, vol. III (20th century AD), Nadeem Yunus Printer/Sheikh Mohd Basheer & Sons, Lahore, 1926 AD, p. 631, Formulation ID: JA6/610C3, Formulation name: Dawa Barae Ziabetas.

Agasthiyar; Agathiar vaithiam 600. Pub & Ed. Anonymous, p. 8, Formulation ID: PD04/07, Formulation Name: Kaantha Chendooram-2.

Rasatantrasarah Evam Siddhaprayogasamgrahah; Part II; Krishan Gopal Ayurveda Bhawan; Edn 8th; 1990 (This book contains back references from 1000 BC to 20th century), pp. 15-16., Formulation ID: RS21/16A, Formulation Name: Naga Bhasma-01.

Rasayogaratnakarah—Translated by Pammi Satyanarayana Sastry, Edited by Koppula Hemadri, 1st Edn. 2005, Dr. Achanta Lakshmipathi Ayurveda Library Trust, 2-Geeta Apartments, New Ayodhyanagar, (Vijayawada), pp. 100-101, Formulation ID: VK6/65, Formulation Name: Vangarajiya Rasa.

Govinda Dasa:Bhaisajya Ratnavali—Edited by Rajeshvaradutta Shastri, Translated by Ambikaduttashastri: Chaukhamba Sanskrit Sansthan, Varanasi, Edn. 14th, 2001 (This book contains back references from 1000 BC to 18th century), p. 828, Formulation ID: AK/4264, Formulation Name: Sasisekhararasah.

Third Party Observation with Annexes I through III issued to European application No. 06714846.0 on Mar. 23, 2011.

* cited by examiner dichroanone (Patent document 12), antiallergic agents (Patent document 13), and so forth. However, effect of plants of the genus *Aloe* on functions of the pancreatic endocrine gland cells is not known.

METHOD FOR IMPROVING PANCREATIC FUNCTIONS

RELATED APPLICATIONS

This application is the U.S. National Phase under 35 U.S.C. §371 of International Application PCT/JP2006/303709, filed Feb. 28, 2006, which was published in a non-English language, which claims priority to Japanese Patent Application No. 2005-144385, filed May 17, 2005.

TECHNICAL FIELD

The present invention relates to a drug and food or drink for improving pancreatic functions, which contains a compound that can be safely ingested and has an effect for protecting pancreatic endocrine gland cells or improving functions of the pancreatic endocrine gland cells.

BACKGROUND ART

The pancreas is an organ constituted by endocrine gland tissues called the pancreas islets (Langerhans islets) and exocrine gland tissues secreting digestive enzymes. The β cells, α cells, δ cells, pancreatic polypeptide cells, and so forth exist in the Langerhans islets, and they greatly affect the control of blood glucose and metabolism. Among these, the β cells play a particularly important role as cells producing insulin.

Diabetes mellitus is a highly frequently observed metabolic disorder recognized in 10% of Japanese adults. According to the epidemiology of the β cell dysfunction of the pancreas, which is considered one of the causes of diabetes mellitus, while the β cell dysfunction is of course observed in individuals with borderline type hyperglycemia, individuals exhibiting normal glucose tolerance also include individuals exhibiting clearly reduced β cell functions at a rate of 30%. Moreover, it is said that adults who lead average social life in present-day Japan highly frequently causes insulin resistance more or less, and it is considered that, as for persons suffering from insulin resistance, in those who do not suffer from β cell dysfunction, the blood glucose level does not increase, and in those who suffer from β cell dysfunction, the blood glucose level increases from a level corresponding to normal glucose tolerance to a level corresponding to borderline type hyperglycemia (Non-patent document 1).

At present, although therapies for promoting spontaneous recovery of the pancreatic functions based on removal of causative pathological conditions or factors are used for pancreatic function disorder, any therapeutic method or agent for positively restoring pancreatic functions once degraded has not been used so far, and agents for protecting pancreatic cells or agents for improving damaged pancreatic cells are desired in the clinical field.

The pancreatic function disorder means a pathological condition that the endocrine or exocrine gland functions of the pancreas are lowered or abnormally enhanced.

As the prior art of agents for curing pancreatic function disorder, those containing neurotrophic factors such as BDNF as an active ingredient (Patent document 1), those containing glycerol derivatives as an active ingredient (Patent document 2), pancreatic function improving agents containing betacellulin proteins or muteins thereof (Patent document 3), and so forth. It has been so far considered that BDNF is released from the central end of small DRG neuron with other transmitters at the time of inflammation or nerve damage, and involved in promotion of pain signal transduction via tyrosine phosphorylation of the NMDA receptor on the dorsal horn cells (Non-patent document 2), and thus it is considered to be restricted for actual use.

Further, the glycerol derivatives disclosed in Patent document 2 are the compounds described in Patent document 4, and are agents having antiplatelet-activating factor (PAF) activity for therapeutic and prophylactic treatment of DIC, shock, allergy, acute pancreatitis, brain twitch at the time of subarachnoid haemorrhage, and so forth, and they are also found to have an organopathy preventing, curing and improving effect for preventing, curing and improving organopathy caused in processes of preservation of organ in ischemic condition, blood flow obstruction caused by post-graft blood reperfusion or surgery, and so forth. However, it is hard to say that these agents are suitable for chronic pancreatic diseases without these symptoms.

Moreover, the pancreatic function improving agents containing betacellulin proteins or muteins thereof disclosed in Patent document 3 also have an action of acting on undifferentiated pancreatic stem cells and thereby promoting differentiation of them into the pancreatic β cells producing insulin, and an action of inducing differentiation of undifferentiated stem cells into other cells of the pancreas such as F cells producing pancreatic polypeptides, and the effect cannot be expected under a condition that immature cells are depleted. In addition, although mRNAs of these proteins are detected in various organs other than the brain, for example, liver, kidney, pancreas, etc., the details of the functions thereof are not clarified almost at all, and therefore it cannot be said that they can be immediately used for clinical cases.

As techniques of using a triterpene glycoside as an active ingredient, for example, a diabetes preventing agent containing a glycoside extracted from *Gymnema inodorum* as an active ingredient (Patent document 5), a metabolism improving method and a composition therefor containing corosolic acid extracted from banaba as an active ingredient (Patent document 6), a lipase inhibitor (Patent document 7) and a triterpene derivative having an immunosuppressing activity (Patent document 8) have been disclosed.

Furthermore, it has been disclosed that compounds having a lanostane skeleton or 3,4-secolanostane skeleton have an insulin action enhancing activity (Patent document 9). The effect of these compounds is to enhance the insulin action in regulation of adipocyte differentiation, and the effect thereof on pancreatic diseases remains unknown.

Furthermore, compounds selected from the group consisting of 24-alkylcholesten-3-ones and 24-alkylcholestan-3-ones that have no double bond in the basic steroid skeleton, or 5-campestene-3-ones that have double bond between 5 and 6 position which is different from the compound of the present invention have been disclosed as hypoglycemic agents (Patent document 10).

Meanwhile, lophenol (one of the stereoisomers of 4-methyl-cholest-7-en-3-ol) has been known to be an intermediate of the biosynthetic pathway starting from squalane in plants (Non-patent document 3). As for prior arts of this compound, however, there is only a reference concerning the biosynthetic system of lophenol (Non-patent document 4), and the use of the compound is not known at all.

The genus *Aloe* in the family Liliaceae is a group of plants including *Aloe* vera (*Aloe barbadensis* Miller) and *Aloe arborescens* (*Aloe arborescens* Miller var. *natalensis* Berger) and so forth, and they are empirically known to have various efficacies. The prior arts regarding the use of plants of the genus *Aloe* include immunomodulating polysaccharides (Patent document 11), immunosuppression improving agents containing a butanol fraction of an *aloe* extract or aloin (Patent document 12), HSP60 family protein synthesis suppressing agents containing aloin derivatives (Patent documents 13 to 15), protein having lectin activity derived from *aloe* leaf-skin (Patent document 16) and arts regarding improvement of blood glucose levels (Non-patent document 5 to 7, Patent document 17 to 20) and so forth.

[Patent document 1] International Publication No. WO 00/62796
[Patent document 2] Japanese Patent Laid-open No. 07-285866
[Patent document 3] Japanese Patent Laid-open No. 09-188630
[Patent document 4] Japanese Patent Laid-open No. 10-045604
[Patent document 5] Japanese Patent Laid-open No. 05-247086
[Patent document 6] Japanese Patent Laid-open No. 2002-205949
[Patent document 7] Japanese Patent Laid-open No. 09-040689
[Patent document 8] Japanese Patent Laid-open No. 11-511482
[Patent document 9] Japanese Patent Laid-open No. 10-330266
[Patent document 10] Japanese Patent Laid-open No. 2003-048837
[Patent document 11] Japanese Patent Laid-open No. 2001-520019
[Patent document 12] Japanese Patent Laid-open No. 08-208495
[Patent document 13] Japanese Patent Laid-open No. 10-120576
[Patent document 14] Japanese Patent Laid-open No. 10-045604
[Patent document 15] Japanese Patent Laid-open No. 10-036271
[Patent document 16] Japanese Patent Laid-open No. 09-059298
[Patent document 17] Japanese Patent Laid-open No. 60-214741
[Patent document 18] Japanese Patent Laid-open No. 2003-286185
[Patent document 19] U.S. Pat. No. 4,598,069
[Patent document 20] U.S. Patent Application Publication No. 2003/0207818
[Non-patent document 1] "Insulin Resistance," Diabetes Mellitus current library, Bunkodo, Apr. 17, 2004
[Non-patent document 2] Brain Res Rev, Vol. 40, pp. 240-249, 2002
[Non-patent document 3] Yamada A., "Experimental Methods of Biochemistry", Vol. 24, Experimental Methods for Fat and Lipid Metabolism, p. 174, Gakkai Shuppan Center, 1989
[Non-patent document 4] Chem. Pharm. Bull., pp. 624-626, 1993
[Non-patent document 5] Phytomedicine, Vol. 3, pp. 245-248, 1996
[Non-patent document 6] Phytotherapy Research, Vol. 15, pp. 157-161, 2001
[Non-patent document 7] Phytotherapy Research, Vol. 7, pp. 37-42, 1993

DISCLOSURE OF THE INVENTION

An object of the present invention is to provide a drug and food or drink suitable for protecting pancreatic endocrine gland cells or improving functions of the pancreatic endocrine gland cells, which does not contain unfavorable ingredients for a drug and food or drink, from a raw material that can be safely ingested from experiential viewpoint for food and is readily obtained.

The inventors of the present invention assiduously studied in order to achieve the foregoing object. As a result, they found that a compound having a structure similar to that of lophenol contained in a wide range of plants could be safely ingested and had an activity for improving pancreatic functions. The present invention was accomplished on the basis of the above finding.

That is, the present invention provides a drug for improving pancreatic functions, which contains a compound represented by the following general formula (1) as an active ingredient:

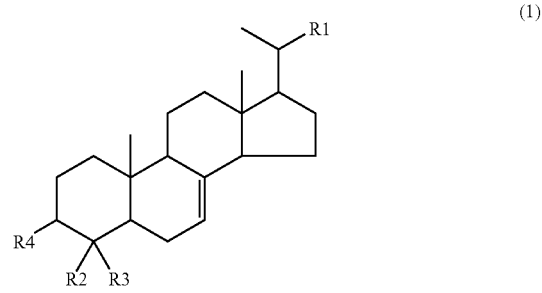

In the formula, R1 represents a straight or branched alkyl group having 5 to 16 carbon atoms, which may contain no double bond or 1 or 2 double bonds and may contain a hydroxyl group and/or a carbonyl group, R2 and R3 each independently represent a hydrogen atom, an alkyl group having 1 to 3 carbon atoms or a substituted alkyl group having 1 to 3 carbon atoms, and R4 forms C=O with the carbon atom constituting the ring or represents —OH or —OCOCH$_3$.

According to a preferred embodiment, one of R2 and R3 is a hydrogen atom, the other is methyl group, and R4 is a hydroxyl group.

According to a preferred embodiment of the drug of the present invention, the improvement of pancreatic functions is to protect pancreatic endocrine gland cells or to improve pancreatic endocrine gland cell functions.

Further, according to a preferred embodiment, in the aforementioned drug and food or drink, R1 is represented by any one of the following formulas:

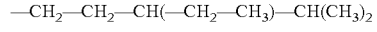

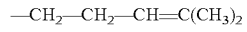

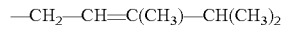

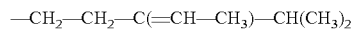

(wherein Ra and Rb is any of —H, —OH, or —CH$_3$)

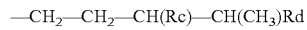

(wherein Rc and Rd is any of —H, —OH, or —CH$_3$)

Furthermore, according to a preferred embodiment, the aforementioned compound contained in the aforementioned drug and food or drink is selected from the group consisting of 4-methyl-cholest-7-en-3-ol, 4-methyl-ergost-7-en-3-ol and 4-methyl-stigmast-7-en-3-ol.

Further, according to a preferred embodiment, the aforementioned drug contains 0.001 to 10% by dry mass of the aforementioned compound.

Further, according to a preferred embodiment, the aforementioned food or drink contains 0.0001 to 1% by dry mass of the aforementioned compound.

The present invention further provides a drug for improving pancreatic functions, which contains a composition consisting of an organic solvent extract or hot water extract of a plant or a fraction thereof containing a compound represented by the aforementioned general formula (1) and containing 0.001 to 10% by dry mass of the aforementioned compound as an active ingredient, or food or drink for improving pancreatic functions, which contains a composition containing 0.0001 to 1% by dry mass of the aforementioned compound as an active ingredient. According to a preferred embodiment of the drug of the present invention, the improvement of pancreatic functions is to protect pancreatic endocrine gland cells or to improve pancreatic endocrine gland cell functions.

The aforementioned plant used for the aforementioned drug and food or drink is preferably a plant of the family Liliaceae, and according to a particularly preferred embodiment, the aforementioned plant of the family Liliaceae is a plant classified into the genus *Aloe*.

The present invention provides the aforementioned food or drink attached with an indication that the food or drink is used for improving pancreatic functions.

Hereafter, the aforementioned drug and food or drink is also generically referred to as "the drug and food or drink of the present invention."

The present invention further provides use of a compound represented by the aforementioned general formula (1) or a composition containing the same in the production of a drug for improving pancreatic functions. According to a preferred embodiment of the use of the present invention, 0.001 to 10% by dry mass of the aforementioned compound is contained. According to a preferred embodiment of the use of the present invention, the improvement of pancreatic functions is to protect pancreatic endocrine gland cells or to improve pancreatic endocrine gland cell functions.

The present invention further provides a method for improving pancreatic functions, which comprises administering a compound represented by the aforementioned chemical formula (1) or a composition containing the same to a subject whose pancreatic functions are to be improved. According to a preferred embodiment of the method of the present invention, the improvement of pancreatic functions is to protect pancreatic endocrine gland cells or to improve pancreatic endocrine gland cell functions. Further, according to a preferred embodiment of the method of the present invention, the aforementioned composition contains 0.001 to 10% by dry mass of the aforementioned compound.

BEST MODE FOR CARRYING OUT THE INVENTION

Hereafter, preferred embodiments of the present invention will be explained in detail. However, the present invention is not limited to the following preferred embodiments, and the preferred embodiments can be freely modified within the scope of the present invention.

According to an embodiment, the drug and food or drink of the present invention contains a compound represented by the aforementioned general formula (1) having an activity for improving pancreatic functions, especially protecting pancreatic endocrine gland cells or improving functions of pancreatic endocrine gland cells (hereinafter also be referred to as "the compound of the present invention") as an active ingredient. According to another embodiment, the drug and food or drink of the present invention comprises a composition containing an organic solvent extract or a hot water extract of a plant or a fraction thereof containing the compound of the present invention as an active ingredient.

In the aforementioned general formula (1), it is preferred that R1 represents a straight or branched alkyl group having 5 to 16 carbon atoms, which may contain no double bond or 1 or 2 double bonds, R2 and R3 each independently represent a hydrogen atom, an alkyl group having 1 to 3 carbon atoms or a substituted alkyl group having 1 to 3 carbon atoms, and R4 forms C=O with the carbon atom constituting the ring or represents —OH or —OCOCH$_3$. As the aforementioned alkyl group having 1 to 3 carbon atoms, methyl group, ethyl group and so forth are preferred, and methyl group is particularly preferred.

The aforementioned R1 is preferably any one of the groups represented by the following formulas:

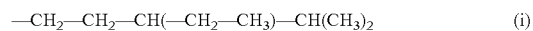  (i)

  (ii)

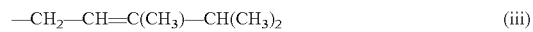  (iii)

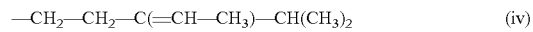  (iv)

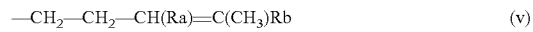  (v)

(wherein Ra and Rb is any of —H, —OH, or —CH$_3$)

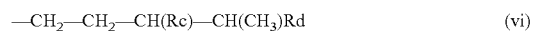  (vi)

(wherein Rc and Rd is any of —H, —OH, or —CH$_3$)

Further, it is preferred that one of R2 or R3 is a hydrogen atom, and the other is a methyl group. Further, it is preferred that R4 is a hydroxyl group.

The most preferred compounds as the aforementioned compound are those represented by the following formulas, 4-methyl-cholest-7-en-3-ol (formula (2)), 4-methyl-ergost-7-en-3-ol (formula (3)) and 4-methyl-stigmast-7-en-3-ol (formula (4)).

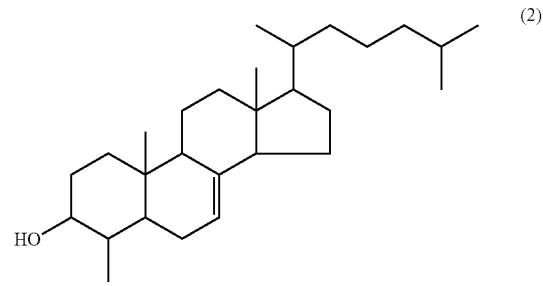

(2)

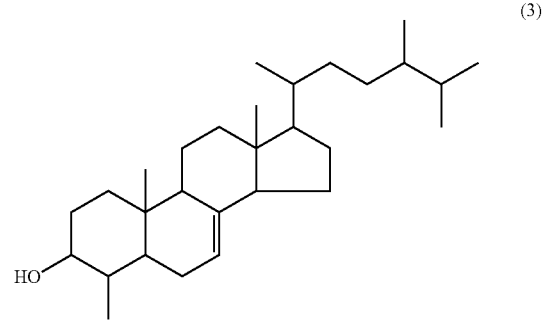

(3)

-continued (4)

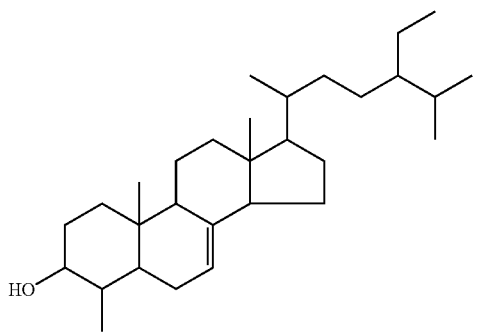

That is, 4-methyl-cholest-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (vi) (Rc represents —H, and Rd represents —CH$_3$). 4-Methyl-ergost-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (vi) (Rc and Rd both represent —CH$_3$). Further, 4-methyl-stigmast-7-en-3-ol is a compound represented by the aforementioned general formula (1) wherein one of R2 and R3 is a hydrogen atom, the other is methyl group, R4 is a hydroxyl group, and R1 is a group represented by the aforementioned formula (i).

The drug and food or drink of the present invention may contain one type or two or more arbitrary types of the aforementioned compounds.

It is known that lophenol is contained in plants, and the compound of the present invention can be produced according to the known method for producing lophenol (Yamada A., "Experimental Methods of Biochemistry", Vol. 24, Experimental Methods for Fat and Lipid Metabolism, p. 174, Gakkai Shuppan Center, 1989). The compound of the present invention can be obtained by, for example, extracting the compound from a plant containing the same using a method such as extraction with an organic solvent or extraction with hot water and purifying the obtained extract. In the present invention, although the compound of the present invention may be purified, a composition such as a plant extract or a fraction thereof may also be used so long as it contains an effective amount of the compound.

Examples of the aforementioned plant include a plant belonging to the family Liliaceae. Examples of the plant belonging to the family Liliaceae include plants belonging to the genus *Aloe* or *Allium*. Examples of the plants of the genus *Aloe* include *Aloe* vera (*Aloe barbadensis* Miller), *Aloe ferox* Miller, *Aloe africana* Miller, *Aloe arborescen* Miller var. *natalensis* Berger, *Aloe spicata* Baker and so forth. In the production of the compound of the present invention or a composition containing the same, although the whole of the aforementioned plant may be used, it is preferable to use mesophyll (clear gel portion) thereof. Such a plant or a part thereof is disrupted preferably by using a homogenizer or the like and thereby liquefied, and the compound of the present invention or a composition containing the same is extracted from the disruption product by using an organic solvent or hot water. Examples of the organic solvent include alcohols such as methanol, ethanol and butanol; esters such as methyl acetate, ethyl acetate, propyl acetate and butyl acetate; ketones such as acetone and methyl isobutyl ketone; ethers such as diethyl ether and petroleum ether; hydrocarbons such as hexane, cyclohexane, toluene and benzene; halogenated hydrocarbons such as carbon tetrachloride, dichloromethane and chloroform; heterocyclic compounds such as pyridine; glycols such as ethylene glycol; polyhydric alcohols such as polyethylene glycol; nitrile solvents such as acetonitrile, mixtures of these solvents and so forth. Further, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform: methanol=about 25:1. Further, when a hexane/ethyl acetate mixture (4:1) is used in reverse phase silica gel column chromatography as an elution solvent, the compound of the present invention is eluted in a fraction eluted at an early stage.

The obtained fraction can be further purified by HPLC or the like.

Further, the compound used for the present invention may also be produced by a chemical synthesis method or a biological or enzymatic method using microorganisms, enzymes or the like.

Whether a compound or a composition containing the same obtained as described above actually contains the compound of the present invention can be confirmed by, for example, mass spectrometry (MS), nuclear magnetic resonance (NMR) spectroscopy or the like.

The compound of the present invention has a pancreatic function improving action, in particular, pancreatic endocrine gland cell protecting action or pancreatic endocrine gland cell function improving action. It can be used as an active ingredient of a drug and food or drink for improving pancreatic functions, in particular, protecting pancreatic endocrine gland cells or improving pancreatic endocrine gland cell functions. In the present invention, protection of pancreatic endocrine gland cells means to protect the pancreatic endocrine gland cells from denaturation due to various causes, or to prevent decrease of the insulin production ability of the pancreatic endocrine gland cells. Further, improvement of pancreatic endocrine gland cell functions means to enhance the insulin production ability of the pancreatic endocrine gland cells of which insulin production ability decreases. Denaturation of pancreatic endocrine gland cells, or protection of pancreatic endocrine gland cells or improvement of pancreatic endocrine gland cell functions can be evaluated by microscopic observation of a pancreatic tissue section of an animal or measurement of serum insulin level.

By the aforementioned actions, the compound of the present invention can prevent decrease of the insulin production ability of pancreatic endocrine gland cells, or enhance the insulin production ability of pancreatic endocrine gland cells of which insulin production ability decreases.

As for the db/db mice used in the examples mentioned later, it is known that affection of the pancreas is observed in them with aging in terms of week (Science, 153, 1127-1128, 1966). Although it has been reported that if N-acetyl-L-cysteine, vitamin C and vitamin E as compounds having an anti-oxidation action are administered to these mice in combination, decrease of the β cell number in the pancreas can be partially prevented (Diabetes, 48, 2398-2406, 1999), even the dose of only N-acetyl-L-cysteine is 100 g/60 kg, and it is expected that administration in extremely large doses is required. In contrast, according to the present invention, it can be expected that the pancreatic endocrine gland cell protecting action or the pancreatic endocrine gland cell function improving action can be attained with a small dose.

The drug of the present invention can be used as an active ingredient of agents for a prophylactic treatment or therapeutic treatment of diseases caused by hypofunction of pancreatic endocrine gland cells, for example, pancreatic function disorder in acute pancreatitis, chronic pancreatitis, type I diabetes mellitus, and type II diabetes mellitus, pancreatic hypofunction associating with senile decrease of insulin secretion, and so forth. Moreover, since the compound of the present invention exhibits low toxicity, it can also be used together with an antitumor agent in a treatment of pancreatic cancer. Preferably, an agent used for improving hyperglycemia among the diseases accompanying decrease in insulin production ability is not encompassed within the scope of the drug of the present invention.

Furthermore, because leaf-skin of *Aloe* vera contains barbaloin and *aloe*-emodin having a laxative action, it is conventionally considered to be unfavorable as a drug and food or drink for which laxative action is not expected. Therefore, it is preferred that the composition containing the compound of the present invention does not contain these ingredients. Further, mesophyll of *Aloe* vera and a disruption product thereof may also be used as an active ingredient of a drug for protecting pancreatic endocrine gland cells or improving pancreatic endocrine gland cell functions.

The compound of the present invention can be used as an active ingredient of the drug and food or drink of the present invention as it is. Further, an organic solvent extract or a hot water extract of a plant or a fraction thereof containing the compound of the present invention (hereinafter referred to as "extract etc.") may also be used as an active ingredient of the drug and food or drink. In this case, the aforementioned extract etc. to be contained in the drug preferably contains 0.001 to 10% by dry mass, more preferably 0.01 to 1% by dry mass, particularly preferably 0.05 to 1% by dry mass, of the compound of the present invention. Further, the aforementioned extract etc. to be contained in the food or drink preferably contains 0.0001 to 1% by dry mass, more preferably 0.001 to 1% by dry mass, particularly preferably 0.005 to 1% by dry mass, of the compound of the present invention. The aforementioned extract etc. may contain two or more types of the compound of the present invention. Further, the aforementioned extract etc. may be a solution, or can also be lyophilized or spray-dried in a conventional manner and stored or used as powder.

As the drug of the present invention, the compound of the present invention or a composition containing the same per se, or the compound of the present invention or a composition containing the same combined with a pharmaceutically acceptable carrier can be orally or parenterally administered to a mammal including human. In the drug of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate, hydrobromate and sulfate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the drug of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual therapeutic or preventive drugs for diseases of internal organs such as pancreas as pharmaceutical carriers such as excipients, binders, disintegrating agents, lubricants, stabilizers, flavoring agents, diluents, surfactants and solvents for injection and so forth can be used. Furthermore, so long as the effect of the present invention is not degraded, the compound of the present invention or a composition containing the same can be used in combination with other drugs having pancreatic disease improving or preventing effect.

Although the amount of the compound of the present invention or a composition containing the same contained in the drug of the present invention is not particularly limited and can be suitably selected, the amount may be, for example, 0.001 to 10% by mass, preferably 0.01 to 1% by mass, particularly preferably 0.05 to 1% by mass, in terms of the amount of the compound of the present invention.

Furthermore, with the drug of the present invention, various diseases, complications and so forth resulted from hypofunction of pancreatic endocrine gland cells can be prevented, and risks of these diseases, complications and so forth can be reduced.

Examples of such various diseases and complications resulted from hypofunction of pancreatic endocrine gland cells include nerve disorder, nephropathy, retinopathy, cataract, macrovascular disease, diabetes mellitus and so forth.

The administration time of the drug of the present invention is not particularly limited and can be suitably selected according to the method for treating an objective disease. Furthermore, the administration route is preferably determined depending on the dosage form, age, sex and other conditions of patients, severity of symptoms of patients and so forth.

The dose of the active ingredient in the drug of the present invention is suitably selected depending on the dosing regimen, age and sex of patients, severity of disease, other conditions of patients and so forth. The amount of the compound of the present invention as an active ingredient is usually selected from the range of, preferably 0.001 to 50 mg/kg/day, more preferably 0.01 to 1 mg/kg/day, as a tentative dose. Furthermore, when the composition of the present invention is used, the dry weight of the composition is selected from the range of, preferably 0.1 to 1000 mg/kg/day, more preferably 1 to 100 mg/kg/day, as a tentative amount. In any case, the dose can be administered once daily or several times as divided portions.

The compound of the present invention or the extract etc. containing the same can be added to food or drink. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added.

The amount of the compound of the present invention or the extract etc. containing the same contained in the food or drink of the present invention is not particularly limited and can be suitably selected. For example, the compound of the present invention or the extract etc. containing the same is contained in the food or drink in an amount of 0.0001 to 1% by mass, preferably 0.001 to 1% by mass, particularly preferably 0.005 to 1% by mass, in terms of the amount of the compound of the present invention.

The food or drink of the present invention can be used for various applications utilizing the pancreatic endocrine gland cell protecting effect or pancreatic endocrine gland cell function improving effect. For example, it can be used as food or drink suitable for "those who have low production of insulin", "those who have low function of insulin", "those who are getting concerned about their functions of pancreas", food or drink useful for decreasing or eliminating risk factors of lifestyle-related diseases such as diabetes mellitus caused by hypofunction of pancreas and pancreatitis caused by excessive ingestion of alcohol and stress.

As for the food or drink of the present invention, the expression "protection of pancreatic endocrine gland cells or improvement of pancreatic endocrine gland cell functions" means that improvement or prevention of various health damages resulted from hypofunction of pancreatic endocrine gland cells, and "protection of Langerhans islet functions", "improvement of Langerhans islet functions", "protection of β cell functions", "improvement of β cell functions", "enhancement of insulin production", "prevention of decrease of insulin production", "enhancement of insulin activity", "prevention of decrease of insulin activity" and so forth are exemplified in the present invention as terms having a meaning similar to that of the aforementioned "protection of pancreatic endocrine gland cells or improvement or pancreatic endocrine gland cell functions".

Furthermore, the food or drink of the present invention is useful for a prophylactic treatment of a disease resulted from hypofunction of pancreatic endocrine gland cells, for example, pancreatic function disorder in acute pancreatitis, chronic pancreatitis, type I diabetes mellitus, and type II diabetes mellitus, hypofunction of pancreas associating with senile decrease in insulin and so forth. Furthermore, the food or drink of the present invention can be used for a prophylactic treatment of various diseases, complications and so forth resulted from hypofunction of pancreatic endocrine gland cells, and can decrease risks of these diseases, complications and so forth. Furthermore, because the compound of the present invention exhibits low toxicity, the food or drink of the present invention is also useful for a patient administered with an antitumor agent in a treatment of pancreas cancer.

Examples of such various diseases and complications resulted from hypofunction of pancreatic endocrine gland cells include nerve disorder, nephropathy, retinopathy, cataract, macrovascular disease, diabetes and so forth.

The food or drink of the present invention is preferably marketed as food or drink attached with an indication that the food or drink is used for protection of pancreatic endocrine gland cells or improvement of pancreatic endocrine gland cell functions, for example, "food or drink containing a compound having a pancreatic endocrine gland cell protecting effect or a pancreatic endocrine gland cell function improving effect indicated as 'For protection of pancreatic endocrine gland cells or improvement of pancreatic endocrine gland cell functions'", "food or drink containing a plant extract indicated as 'For protection of pancreatic endocrine gland cells or improvement of pancreatic endocrine gland cell functions'", "food or drink containing *Aloe* vera extract indicated as 'For protection of pancreatic endocrine gland cells or improvement of pancreatic endocrine gland cell functions'" and so forth.

The wording used for such an indication as mentioned above is not necessarily be limited to the expression "For protection of pancreatic endocrine gland cells or improvement of pancreatic endocrine gland cell functions", and any other wording expressing the pancreatic endocrine gland cell protecting effect or pancreatic endocrine gland cell function improving effect of course falls within the scope of the present invention. As such a wording, for example, an indication based on various uses allowing consumers to recognize the pancreatic endocrine gland cell protecting effect or pancreatic endocrine gland cell function improving effect is also possible. Examples include indications of "Suitable for those who have low production of insulin", "Suitable for those who have low function of insulin", "Useful for decrease or elimination of risk factors (risks) of lifestyle-related diseases such as diabetes mellitus caused by reduction of insulin activity or production, pancreatitis caused by excessive ingestion of alcohol and stress" and so forth.

The aforementioned term "indication" includes all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth.

The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, others documents and so forth.

Examples of the indication further include indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

EXAMPLES

The present invention will be explained more specifically with reference to the following examples. However, the scope of the present invention is not limited to the following examples.

Preparation Example

In an amount of 100 kg of mesophyll (clear gel portion) of *Aloe* vera was liquefied by using a homogenizer, added with 100 L of an ethyl acetate/butanol mixture (3:1) and stirred.

The mixture was left standing overnight, and then the ethyl acetate/butanol mixture and the aqueous layer were separated to recover the ethyl acetate/butanol mixture. The extract from this ethyl acetate/butanol mixture obtained by concentrating the ethyl acetate/butanol mixture under reduced pressure weighed 13.5 g. A solution of 13 g of this extract dissolved in 1 mL of a chloroform/methanol mixture (1:1) was loaded on a column filled with 400 g of Silica Gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. It was confirmed by normal phase and reverse phase thin layer chromatography (Merck Ltd., Silica Gel 60F254 and RP-18F2543) that, among these fractions, the compound of the present invention existed in the fraction eluted with the mixture of chloroform:methanol=25:1.

This crude purified substance (crude purification product 1) containing the compound of the present invention weighed 3 g. Further, the yields of the crude purification products obtained in the above operation from the fractions eluted with the mixtures of chloroform:methanol=10:1 and 1:1 were 1.17 and 2.27 g, respectively. The solvents of these fractions were removed, then each extract was dissolved in 1 mL of a chloroform/methanol mixture (1:1) and loaded on a column filled with 100 g of Silica Gel 60 to attain adsorption of the components to the column, and then the components were eluted with 1100 mL of a hexane/ethyl acetate mixture (4:1). The eluted fractions were collected as aliquots of 300 mL (fraction A), 300 mL (fraction B) and 500 mL (fraction C) in this order. The yields obtained after removing the solvents from the fractions A, B and C were 0.6 g, 1.35 g and 0.15 g, respectively.

It was confirmed by normal phase and reverse phase thin layer chromatography that the compound of the present invention had been concentrated in the fraction A (crude purification product 2). This crude purification product 2 was further separated by HPLC using COSMOSIL C18 (Nacalai Tesque, Inc.) with a chloroform/hexane mixture (85:15) to obtain 1.3 mg of compound 3 (4-methyl-cholest-7-en-3-ol), 1.2 mg of compound 4 (4-methyl-ergost-7-en-3-ol) and 1 mg of compound 5 (4-methyl-stigmast-7-en-3-ol). The structures of these compounds were confirmed by MS and NMR.

Test Example 1

In this test, the endocrine gland cell functions (insulin production ability) protecting action of compounds having a lophenol skeleton was evaluated by using db/db mice known as a model animal of pancreatic hypofunction or pancreatic tissue dysfunction.

(1) Preparation of Sample 4-methyl-cholest-7-en-3-ol produced in Preparation Example mentioned above was used as test sample 1, 4-methyl-ergost-7-en-3-ol was used as test sample 2, and 4-methyl-stigmast-7-en-3-ol was used as test samples 3.

(2) Test Method

In this test, 6-week old male db/db mice (purchased from Clea Japan, Inc.) were used. These mice were divided into groups, each consisting of 7 animals. Each test sample was dissolved in DMSO, and the concentration was adjusted to 0.1 or 1 µg/mL with physiological saline. The final DMSO concentration was adjusted to 0.2%. The pancreas dysfunction model mice were orally administered with 1 mL of the test sample once a day everyday for 42 days with a sonde. The serum insulin level was measured on the 43rd day of the continuous administration by using Lbis insulin mouse ELISA kit (Shibayagi Co., Ltd).

(3) Test Results

The serum insulin levels on the 43rd day of the continuous administration of the samples are shown in Table 1. When the test sample 1, 2 or 3 was administered at a concentration of 1 µg/animal, the serum insulin levels were as high as 184, 210 and 211% of that observed in the negative test respectively, and thus pancreatic function (insulin production ability) protecting effect by protecting pancreas dysfunction was clearly observed. On the other hand, when it was administered at a concentration of 0.1 µg/animal, any significant pancreatic function protecting effect was not observed. During the administration period, no side-effect was observed at all in view of body weight and pathological findings.

TABLE 1

Serum insulin levels on 43rd day of continuous administration

| Sample | Serum insulin levels on $43^{rd}$ day of administration (ng/mL) | <p relative to negative sample> |
|---|---|---|
| Negative sample | 1.99 ± 0.66 | |
| Test sample 1 (1 µg) | 3.67 ± 0.80 | <0.003*> |
| Test sample 1 (0.1 µg) | 2.33 ± 1.23 | <0.19> |
| Test sample 2 (1 µg) | 4.17 ± 2.23 | <0.04*> |
| Test sample 2 (0.1 µg) | 2.32 ± 1.52 | <0.27> |
| Test sample 3 (1 µg) | 4.20 ± 1.86 | <0.02*> |
| Test sample 3 (0.1 µg) | 2.23 ± 0.68 | <0.17> |

*indicates presence of statistically significant difference.

Test Example 2

In this test, the pancreatic tissue protecting action of compounds having a lophenol skeleton was examined by using db/db mice known as a model animal of pancreatic hypofunction or pancreatic tissue dysfunction.

(1) Preparation of Sample 4-methyl-cholest-7-en-3-ol produced in Preparation Example mentioned above was used as test sample 1, 4-methyl-ergost-7-en-3-ol was used as test sample 2, 4-methyl-stigmast-7-en-3-ol was used as test samples 3. Further, β-sitosterol (Tama Biochemical Co., Ltd.) was used as a control sample.

(2) Test Method

In this test, 6-week old male db/db mice (purchased from Clea Japan, Inc.) were used. These mice were divided into groups, each consisting of 7 animals. Each test sample was dissolved in DMSO, and the concentration was adjusted to 1 μg/mL with physiological saline. The final DMSO concentration was adjusted to 0.2%. The model mice were orally administered with 1 mL of the test sample once a day everyday for 42 days with a sonde. On the 43rd day of the continuous administration, the pancreas was extracted, divided into three portions of upstream, midstream and downstream from the duodenum side, and fixed with a formalin solution, and then paraffin blocks were prepared in a conventional manner. Section slides were prepared from the paraffin blocks, and subjected to hematoxylin-eosin staining. The numbers of Langerhans islets existing on the sections of the 3 position of the pancreas, and area of Langerhans islet having the maximum area on each section were measured by using an ocular micrometer on a microscope ("ECLIPSE E600", NIKON CORP.).

(3) Test Results

The numbers of Langerhans islets in the pancreatic sections on the 43rd day of the continuous administration of the samples are shown in Table 2, and the maximum areas of Langerhans islets on the same day are shown in Table 3. The numbers of Langerhans islets of the mice administered with the test sample 1, 2 or 3 were 188, 159 and 150% of the number of Langerhans islets in the negative sample-administered mice, respectively, and it was found that the numbers were clearly large in the test sample-administered mice. Similarly, the maximum areas of Langerhans islets in the mice administered with the test sample 1 or 2 maintained 3.6, 4 and 2.8 times as large as that observed in the negative test, and thus it was found that reduction of the Langerhans islets due to pancreatic dysfunction was prevented. On the other hand, the numbers and maximum areas of Langerhans islets of the mice administered with the control sample don't show any significant change, and any pancreatic function protecting effect was not observed. From these results, it was revealed that 4-methyl-cholest-7-en-3-ol, 4-methyl-ergost-7-en-3-ol, 4-methyl-stigmast-7-en-3-ol had an action of protecting pancreatic tissues, especially endocrine cells.

TABLE 2

The numbers of Langerhans islets in pancreatic pathologic sections of treated mice

| Sample | The numbers of Langerhans islets in sections on $43^{rd}$ day of administration (piece) | <p relative to negative sample> |
|---|---|---|
| Negative sample | 40.3 ± 9.7 | |
| Test sample 1 (1 μg) | 75.7 ± 24.7 | <0.008*> |
| Test sample 2 (1 μg) | 64.1 ± 9.1 | <0.0003*> |

TABLE 2-continued

The numbers of Langerhans islets in pancreatic pathologic sections of treated mice

| Sample | The numbers of Langerhans islets in sections on $43^{rd}$ day of administration (piece) | <p relative to negative sample> |
|---|---|---|
| Test sample 3 (1 μg) | 60.4 ± 11.6 | <0.004*> |
| Control sample (1 μg) | 42.3 ± 20.1 | <0.8> |

*indicates presence of statistically significant difference.

TABLE 3

Maximum areas of Langerhans islets in pancreatic pathologic sections of treated mice

| Sample | Maximum area of Langerhans islets on administration × $10^3$ ($\mu m^2$) | <p relative to negative sample> |
|---|---|---|
| Negative sample | 44.5 ± 17.7 | |
| Test sample 1 (1 μg) | 160.0 ± 116.0 | <0.04*> |
| Test sample 2 (1 μg) | 178.7 ± 143.4 | <0.005*> |
| Test sample 3 (1 μg) | 122.6 ± 51.4 | <0.006*> |
| Control sample (1 μg) | 69.1 ± 40.6 | <0.18> |

*indicates presence of statistically significant difference.

INDUSTRIAL APPLICABILITY

The drug and food or drink of the present invention can be safely administered or ingested and have activity of protecting pancreatic endocrine gland cells and improving pancreatic endocrine gland cell functions. Further, the active ingredient of the drug and food or drink of the present invention can be produced from a plant that can be safely ingested from an experiential viewpoint for food and is readily available, for example, a plant of the family Liliaceae such as *Aloe* vera (*Aloe barbadensis* Miller).

What is claimed is:

1. A method for treating pancreatitis, which comprises administering 0.001 to 50 mg/kg/day of a compound obtainable from an ethyl acetate/butanol mixture extract or a chloroform/methanol mixture extract of a plant of the family Liliaceae or a fraction thereof to a subject in need of treatment for pancreatitis, wherein the compound is selected from the group consisting of 4-methyl-cholest-7-en-3-ol, 4-methyl-ergost-7-en-3-ol and 4-methyl-stigmast-7-en-3-ol.

* * * * *